(12) United States Patent
Ganter et al.

(10) Patent No.: US 8,437,479 B2
(45) Date of Patent: May 7, 2013

(54) CALIBRATED DIGITAL HEADSET AND AUDIOMETRIC TEST METHODS THEREWITH

(75) Inventors: Declan B. Ganter, Dartry (IE); Fintan J. Graham, Greystones (IE); Martin C. Ganter, Blackrocks (IE)

(73) Assignee: Cleartone Technologies Limited (IE)

( * ) Notice: Subject to any disclaimer, the term of this patent is extended or adjusted under 35 U.S.C. 154(b) by 610 days.

(21) Appl. No.: 12/295,977

(22) PCT Filed: Mar. 29, 2007

(86) PCT No.: PCT/EP2007/002774
§ 371 (c)(1),
(2), (4) Date: Apr. 7, 2010

(87) PCT Pub. No.: WO2007/112918
PCT Pub. Date: Oct. 11, 2007

(65) Prior Publication Data
US 2010/0191143 A1 Jul. 29, 2010

Related U.S. Application Data (60) Provisional application No. 60/788,709, filed on Apr. 4, 2006.

(51) Int. Cl.
*H04R 29/00* (2006.01)
(52) U.S. Cl.
USPC ............ 381/60; 381/58; 381/314; 381/320; 600/559
(58) Field of Classification Search .............. 381/58–60, 381/74, 314, 320; 700/94; 600/559
See application file for complete search history.

(56) References Cited

U.S. PATENT DOCUMENTS 3,809,811 A 5/1974 Delisle et al.
4,471,171 A 9/1984 Koepke et al.
(Continued)

FOREIGN PATENT DOCUMENTS

EP 1261235 11/2002
WO 03/032683 A1 4/2003
WO WO 03/030619 4/2003

OTHER PUBLICATIONS

International Search Report for International Application No. PCT/EP2007/002774 mailed Jun. 11, 2007.
Aug. 9, 2010 Office Action for European Application No. 07 723 718.8.

(Continued)

*Primary Examiner* — Disler Paul
(74) *Attorney, Agent, or Firm* — Katten Muchin Rosenman LLP (57) ABSTRACT

A digital headset system for use in audiometric testing. The headset system includes a stored calibration reference relating the exact frequency and volume response of each speaker to analog input signals. A microprocessor accesses the calibration reference to determine the required analog signal needed to produce the desired sound. An on-board digital to analog converter generates the required analog signal and transmits it to the speaker. The headset is used with software based audiometric test methods that allow the generation of an electronic user hearing profile. The user hearing profile may be used to re-program an audio emitting device to function in a customized manner. The user hearing profile may be overlaid on a partner hearing profile in order to emulate for the partner how sounds are perceived by the user. The test methods may be self-administered or administered by a healthcare professional.

11 Claims, 5 Drawing Sheets

U.S. PATENT DOCUMENTS

| | | |
|---|---|---|
| 6,522,988 B1 | 2/2003 | Hou |
| 7,529,545 B2 * | 5/2009 | Rader et al. ............... 455/432.2 |
| 7,961,891 B2 * | 6/2011 | Dorfman et al. ............... 381/58 |
| 2002/0165466 A1 | 11/2002 | Givens et al. |
| 2004/0006283 A1 | 1/2004 | Harrison et al. |
| 2006/0045281 A1 | 3/2006 | Korneluk et al. |

OTHER PUBLICATIONS

Nov. 2, 2011 Examiner's Amendment for European Application No. 07 723 718.8.

Patentable claims for EP Patent Application No. 07 723 718.

* cited by examiner

Figure 5

CALIBRATED DIGITAL HEADSET AND AUDIOMETRIC TEST METHODS THEREWITH

CROSS-REFERENCE TO RELATED APPLICATIONS

This application is a National Phase Application of PCT International Application No. PCT/EP2007/002774, International Filing Date Mar. 29, 2007, entitled "Calibrated Digital Headset And Audiometric Test Methods Therewith", Published on Oct. 11, 2007 as International Publication No. WO 2007/112918, which claims priority of U.S. Provisional Patent Application No. 60/788,709, Filed on Apr. 4, 2006, which is incorporated herein by reference in its entirety.

FIELD OF THE INVENTION

The invention relates to the field of audiometric testing and analysis. More particularly, the invention relates to a calibrated digital headset for use with computer based audiometric test methods that may be either self-administered or administered by a trained test provider, such as a healthcare professional or industrial screener. Methods of audiometric testing using the headset and methods of adjusting the output of an audio emitting device to account for the hearing impairment of a particular listener are also disclosed.

BACKGROUND

In conventional audiometric testing, a test recipient is required to be assessed by a trained test provider, typically a healthcare professional, using an expensive and complicated piece of analog test equipment. The analog test equipment consists of a calibrated system comprising an analog headset and an analog tone generator capable of generating pure tone signals at several test frequencies and volume levels. The test frequencies and volume levels are as prescribed by relevant test standards in the jurisdiction in which the test is being conducted.

The entire analog system must be calibrated as a whole and can only be certified for use at the selected calibration test frequencies. This requires both the headset and tone generator to be sent off-site to a certified calibration lab, taking them out of service for a prolonged period of time, and limits the testing performed with the system to only the prescribed frequencies. There is therefore no way to test at intermediate frequencies in order to better discriminate a region of hearing loss. In addition, the calibration of the analog equipment is often only performed at one loudness level, potentially leading to the equipment producing inaccurate loudness levels at other volumes. There is no means to periodically check the calibration of a particular headset, nor is there a means to compensate for a drift in calibration in between offsite re-calibrations. It is not possible to interchange headsets with a pre-calibrated tone generator in the event that a particular headset becomes defective. The test must be performed and interpreted by a healthcare professional in order to identify regions of hearing loss and to specify an appropriate hearing aid device or other appropriate course of action. There is no way of administering a hearing self-test, particularly in the home, and no means of sharing the self-test data with trained professionals. There is currently no way to emulate the effect of a hearing aid for the test recipient, especially in typical real world environments, and no way to emulate for a third party (eg: spouse or partner of the test recipient) the way in which sounds are perceived by the test recipient. There is currently no way to adjust the audio output of digital audio emitting devices (eg: cell phones, MP3 players, iPod's, computers, etc.) to improve the listening experience of a particular hearing impaired listener.

In order to address some or all of the foregoing problems in the art, there remains a need for an improved audiometric test apparatus, improved audiometric test methods, and improved methods of calibrating audio emitting devices to account for deficiencies in hearing.

SUMMARY OF THE INVENTION

According to the present invention, there is provided a digital headset system for use in audiometric testing comprising: at least one speaker; a digital data interface for connection with a computer; an electronic memory module for storing a unique calibration reference relating to the speaker; a microprocessor for processing digital data corresponding to a desired sound output, the microprocessor able to electronically access the calibration reference to determine the required analog signal to be delivered to the speaker in order to emit the desired sound output; and, a digital to analog converter for delivering the required analog signal to the speaker.

The headset may comprise a plurality of speakers and may comprise one or more speakers for each ear optionally located within a head-mountable housing suitable for placing the speakers on or in the user's ears. The speaker or speakers are capable of emitting a pure tone sound output (along with various other sound outputs) within the audible frequency range to within accepted frequency tolerances for such pure tone signals or sounds. The unique calibration reference relates analog electrical input signals with frequency and volume characteristics of sound outputs from the speaker. For example, the calibration reference may comprise a table relating the above input and output information. Either the table itself may be stored on the electronic memory module or a unique identifier may be stored for use in retrieving the table from another storage location. In cases where there is a plurality of speakers, a unique calibration reference may be provided for each speaker or, alternatively, a single calibration reference having entries for each speaker may be provided.

The electronic memory module preferably maintains data storage when power is interrupted to the memory module and may be user re-programmable. For example, the electronic memory module may comprise a read only memory (ROM) chip such as an electrically erasable programmable read only memory (EEPROM) chip, a flash memory chip, etc. Additional electronic memory modules may be provided to receive and store user uploaded information, for example information relating to a user hearing profile for use in re-programming the headset to function as a customized digital audio headset that automatically compensates for one or more regions of hearing loss within the user's hearing profile, in a manner as will be more thoroughly described hereinafter.

The digital data interface may comprise a cabled connection or a wireless connection. The digital data interface is capable of passing digital signals to the headset at a rate sufficient to allow the headset to function as an audiometric test device. The digital data interface may comprise a USB connection or other suitable connection to the computer. The digital data interface may include a component that may be separated from the headset for use in completing a wireless connection, for example a USB Bluetooth® dongle for attachment to a USB port of a computer for transmitting digital data signals to the headset via the Bluetooth® wireless protocol.

The microprocessor may be interconnected with one or more random access memory (RAM) modules that function as a data buffer that first receives the digital data from the computer and stores it until such time as it is needed by the microprocessor (nanosecond to millisecond time scale). The RAM modules may also be used for temporary variable storage by the microprocessor.

The digital to analog converter (DAC) may be 8-bit, 16-bit, 24-bit or floating, as is known in the art. The DAC converts digital signals delivered by the microprocessor to analog electrical signals suitable for delivery to the speaker(s). A digital signal processor (DSP) may optionally be provided between the microprocessor and the DAC or the functions of the DSP may be incorporated within either the microprocessor or DAC. In one embodiment, the electronic memory module, DAC, at least a portion of the digital data interface and optionally the microprocessor and/or any desired buffers or DSP are provided within a small enclosure located either on the head-mountable housing or in proximity to the housing and in electronic communication therewith. For example, for cabled headsets, the enclosure may be provided in line with the digital data interface cable; for wireless headsets, the enclosure may be provided as part of a separate or separable hardware portion of the digital data interface, such as a USB dongle. In another embodiment, the microprocessor and any required buffers or DSP are provided within the computer to which the headset is connected to thereby complete the overall headset system. When located on the housing, the enclosure is preferably lightweight and unobtrusive so as not to interfere with the wearing and use of the headset. To reduce size and simplify performance, some or all of the functions of the microprocessor, DAC, DSP, buffers or a portion of the digital data interface may be provided by one or more application specific integrated circuits (ASIC's) located within the enclosure. Elements of the system may be physically located within separate articles that are electrically interconnected. For example, the housing, enclosure and computer may each contain elements of the system. The system is therefore particularly amenable to being provided in the form of a kit that comprises one or more of the housing, enclosure or computer along with instructions for the interconnection thereof and optionally any necessary cables or ancillary equipment.

The digital headset is advantageous in that only the headset needs to be calibrated, not the entire system, and that a plurality of headsets may be used and/or interchanged with any particular computer based system. Furthermore, the headset can be re-programmed to function as a customized digital audio headset, providing immediate correction for user hearing loss in certain applications (for example, listening to digital multimedia content, such as music or movies, and in voice over IP telephony).

According to another aspect of the invention, there is provided a method of audiometric testing using a calibrated digital headset system, the method comprising: providing a calibrated digital headset system comprising: i) at least one speaker; ii) a digital data interface for connection with a computer; iii) an electronic memory module for storing a unique calibration reference relating to the speaker; iv) a microprocessor for processing digital data corresponding to a desired sound output, the microprocessor able to electronically access the calibration reference to determine the required analog signal to be delivered to the speaker in order to emit the desired sound output; and, v) a digital to analog converter for delivering the required analog signal to the speaker; interconnecting the digital data interface with the computer; administering a software generated audiometric test using the headset, the test comprising the emission of a first set of sound outputs having pre-specified frequency and/or volume characteristics; receiving into the computer user feedback concerning the audibility of the first set of sound outputs; and, generating using the computer a user hearing profile based upon the results of one or more audiometric tests. The hearing profile relates the frequency and volume information of sounds as heard by the test recipient to the frequency and volume information of sounds as emitted by the audiometric test system.

The method may further comprise: administering a follow-up audiometric test using the headset system, the follow-up audiometric test comprising the emission of a second set of sound outputs having frequency and/or volume characteristics selected by the computer and/or healthcare professional to further characterize a region of hearing loss within the user hearing profile; receiving into the computer user feedback concerning the audibility of the second set of sound outputs; and, refining with the computer the user hearing profile based upon the results of one or more follow-up audiometric tests. The second set of sound outputs may comprise a plurality of discrete frequencies selected from between the frequencies employed in the first set of sound outputs in order to further characterize a region of hearing loss located between two or more standard test frequencies. This allows a user or healthcare professional to more accurately map out the required hearing aid characteristics to correct the hearing loss than would otherwise be possible using standard analog techniques.

The method may further comprise re-programming the digital headset system using the user hearing profile to function as a customized headset by: analyzing the user hearing profile with the computer to determine at least one region of hearing loss; determining using the computer the required amplification of frequencies within the region of hearing loss; uploading the required amplification to the headset using the digital data interface; and, electronically storing the required amplification on the digital headset in a data format accessible by the microprocessor. The re-programmed digital headset system is useful in providing immediate hearing loss correction for certain applications and this method can advantageously be performed by the user on one or more digital headsets.

The method may further comprise re-programming an audio emitting digital device using the user hearing profile to function as a customized audio emitting digital device by: analyzing the user hearing profile with the computer to determine at least one region of hearing loss; determining using the computer the required amplification of frequencies within the region of hearing loss; uploading the required amplification to the audio emitting digital device; and, electronically storing the required amplification on the audio emitting digital device in a data format accessible by audio processing circuitry of the device. The audio emitting digital device may comprise a digital music player, such as an iPod or MP3 player, a phone, a digital Dictaphone, an assistive listening device, a home or car stereo, a television set, or the like.

The method may further comprise: analyzing the user hearing profile with the computer to determine at least one region of hearing loss by comparing the user hearing profile with a previously determined partner hearing profile using the computer; for the partner hearing profile, determining using the computer the required amplification or deamplification of frequencies within the region of hearing loss in order to match the partner hearing profile with the user hearing profile; and, using the digital headset system, emitting a series of sounds modified by the required amplification or deamplification in order to audibly emulate for the partner how those sounds are perceived by the user. The term "emulate", as used herein, will be understood by persons skilled in the art to encompass simulation, modeling or otherwise reproducing the sounds experienced by the user for the partner. Allowing a partner, such as a spouse or a healthcare professional, to experience how sounds are perceived by the user is helpful in building an understanding of the difficulties experienced by the user and in allowing the partner to help the user cope with the hearing loss. In addition, the emulation function may be demonstrated using either pre-recorded sound clips, user recorded sound clips, or used in real-time to allow the partner to experience the sounds of daily life as perceived by the user. The method may further comprise generating a visual representation of the user hearing profile using the computer. The visual representation may comprise a diagram of the cochlea illustrating with colour the location(s) of the hearing loss and optionally overlaying in a different colour either a partner's hearing profile or a normal (undamaged) hearing profile. Otoscopic images collected from examination of the user's outer ear area, ear canal, ear drum, etc. can be stored in conjunction with the user hearing profile and may be used in generating a visual representation of the hearing loss. A three-dimensional model of the user's ear and/or ear canal may be generated by the computer. This may be useful in visually illustrating the hearing loss type and/or location, or how normal hearing works, and also in the sizing and fitting of a suitable hearing aid to correct the hearing loss.

The user hearing profile may be stored in a central data depository and may be uploaded or indexed on a central server for access by either the user, the partner, further healthcare professionals, or hearing aid manufacturers. This facilitates further diagnosis and the electronic ordering of customized hearing aid devices based upon the user hearing profile.

The method may further comprise: providing a microphone interconnected with an A/D converter for digitally delivering sound information to the computer; digitally recording speaker outputs using the microphone; and, comparing the digitally recorded outputs with a baseline to determine the need for re-calibration of the headset system. A digital correction obtained from the comparison conducted above may be applied within the computer or the headset to counteract the need for headset re-calibration, thereby extending the period between re-calibrations and improving the accuracy of sound reproduction.

According to yet another aspect of the invention, there is provided a method of modulating the audio output of an audio emitting device using a user hearing profile, the method comprising: analyzing the user hearing profile with the computer to determine at least one region of hearing loss; determining using the computer the required amplification of frequencies within the region of hearing loss; and, applying the required amplification to audio outputs of the audio emitting device. In one embodiment, the method may further comprise: uploading the required amplification to the audio emitting digital device; electronically storing the required amplification on the audio emitting digital device in a data format accessible by audio processing circuitry of the device; and, applying the required amplification to audio outputs of the audio emitting device using the audio processing circuitry of the device. In another embodiment, the method may further comprise: uploading the required amplification to a server on an audio transmission network; relating the required amplification to a personal identifier that can be received by the server; and, applying the required amplification to signals transmitted over the network to a user providing the personal identifier.

BRIEF DESCRIPTION OF THE DRAWINGS

Having summarized the invention, preferred embodiments thereof will now be described with reference to the accompanying figures, in which.

DETAILED DESCRIPTION

Figure 1:
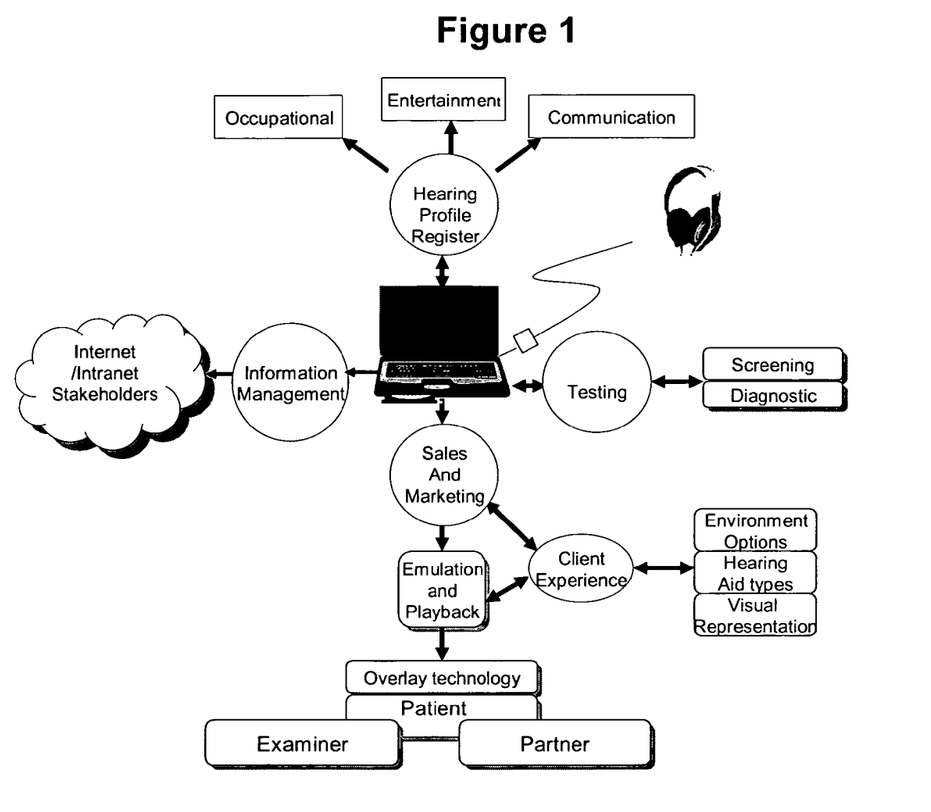
FIG. 1 shows an overview of an audiometric test system comprising a computer and a calibrated digital headset according to the present invention.

Referring to FIG. 1, the overall audiometric test system according to the present invention will be generally described.

A hearing test is either self-administered or administered by a trained test provider, such as a healthcare professional, industrial screener or the like. When administered by a healthcare professional, prior to performing the test, the test recipient (alternatively referred to herein as a user or a subject) is first examined in the ears using an Otoscope to check for noticeable conditions which may cause hearing loss such as infection, wax, foreign object blockage, etc. If an electronic Otoscope is used the health professional can retain a digital image record of the ear canal and eardrum in the computer with the subject's test results. The subject answers a questionnaire to allow the health professional to get a general assessment of the subject's hearing ability based on medical history, lifestyle, activities and hobbies which could affect hearing, such as shooting or physical sports. The questionnaire also covers the subject's activities in the previous 24 to 48 hours to establish exposure to loud noises that might affect the hearing test. The subject is then given clear instructions of how the hearing test is to be performed. The subject is instructed to indicate when the sound (tone) is first heard using the following words or similar:

"I am going to test your hearing by measuring the quietest sounds that you can hear. As soon as you hear a sound (tone), press the response button. Whatever the sound and no matter how faint the sound, press the button as soon as you think you hear it."

These instructions can additionally or alternatively be displayed on a computer screen to be read by the test recipient. The healthcare professional places the headphones on the subject and demonstrates the type of sound (eg: pure tone) that the test system will emit, and how the subject should respond to hearing the sound, for example by providing an input directly to the computer using any suitable I/O device connected to the computer. The health professional then starts the automated test to produce the test signals at the frequencies and intensities as set down in applicable standards for different tests, depending upon the jurisdiction in which the test is being performed.

The test produces a graphical representation of the subjects hearing known as an audiogram which shows the tone frequency on the x-axis and the intensity (loudness) on the y-axis. The response from the subject on the test frequencies used (up to about 11 per ear) are shown as points on the graph which are connected by a line. Alternative graphical representations may also be provided, including for example a representative "normal" hearing profile for a test subject of similar age and gender or an image of the cochlea overlaid in colour to show the damaged area(s).

The computer is able to store and use information gathered from clients and healthcare professionals. By using a networked system, it is possible to build up useful demographic information of hearing loss, hearing aid dispensing and client feedback. The first time a subject presents himself to a health professional using this system, he or she is asked to complete a detailed questionnaire which is then added to the central knowledge database using a unique key identifier. On subsequent visits, this information is retrieved and updated to take account of any hearing related changes that may have occurred with the subject in the interim period.

There are three areas of information gathered and held, namely:
1. general information about the subject, their age, health, hearing issues or problems, hearing aids, occupation, hobbies and so on;
2. information specific to the hearing test performed and the results including a digital hearing profile (added to any existing profiles for this subject), Otoscopic images if required, information on referrals to further tests or consultations; and,
3. information related to specific questionnaires which are controlled and downloaded to the system from a central agency to ascertain more general information on hearing issues and causes from a demographic and socio economic, age, sex and geographic perspective.

By testing subjects in this manner, it is possible to accurately define and retain a digital hearing profile relating to the subject's hearing. This user hearing profile is then used to calculate the optimal adjustments which would improve the hearing of the user without causing further damage to his or her hearing; this is done by a combination of digitally adjusting the areas of loss and fine tuning as a result of experience and feedback.

The user hearing profile can optionally be uploaded to the digital headset and/or any audio emitting digital device to allow customisation and adjustment of sounds for the individual clients. Examples of suitable applications of this technology include the use of personal entertainment systems, phones (mobile and fixed line) and occupational applications and requirements such as call centres and so on. The user hearing profile is optionally uploaded to a central server and provided over a transmission network; for example, the user hearing profile may be used by a phone company to adjust the signal being provided over the phone network to a particular user's telephone. By dialing a personalized access code, any telephone used by a particular user on the network would then emit an audio signal customized with that user's hearing profile.

After the user hearing profile is generated, the basic design of a hearing aid device suitable for correcting the hearing problem can be completed and tested immediately by the user via the digital headset. The user can choose what type of sounds they would like to hear (and compare) and what type of listening environment they are likely to be in when hearing the sounds. Examples of listening environments include, outdoors, indoors in a quiet setting, at a noisy party, etc. Once the listening environment is chosen, the user can audibly hear the difference "before" and "after" the application of adjustment to their hearing profile. Currently this is not possible to do in most test systems due to the limited functionality of existing analog test equipment. The present invention advantageously allows the user to immediately experience the effects of a hearing aid in the chosen listening environment and allows the user to suggest changes or corrections to the design in order to make it function more effectively, before ordering the actual hearing aid device.

Often people getting hearing tests bring a spouse or partner. The partner can also have a test and have their partner hearing profile recorded. Using the method of the present invention, it is then possible to overlay the partner and user hearing profiles to allow the partner to experience sounds as they are perceived by the user and to experience the improvement that the user would realize if fitted with a suitable hearing aid. It is also possible for the hearing professional to overlay their own hearing profile and listen to the quality of the user's hearing for additional diagnostic purposes.

All of these additional facilities mean that the user and partner are more engaged in the hearing test and emulation process, get a much clearer picture of the problems and solutions and can experience how their quality of hearing and therefore lifestyle could be improved. This will help the user and partner to make a more informed and immediate decision to purchase a hearing aid, thereby reducing the current average buying lead-time.

It should be noted that, although the foregoing description is with reference to a test performed by a healthcare professional, the computerized nature of the method lends itself to being performed by the user directly. Computer generated prompts would direct the user to perform the test in the prescribed manner and the computer would analyze the results automatically to determine whether the type of hearing loss fits within known parameters or whether further analysis is required by a trained professional. The automation of the test procedure makes the system amenable to self-serve kiosks that are accessible to the public and/or to in-home diagnostic applications. Further potential applications of the present invention include corporate environments, where it could be used as a screening tool for early hearing loss detection to avoid potentially costly compensation claims later on.

Figure 2:
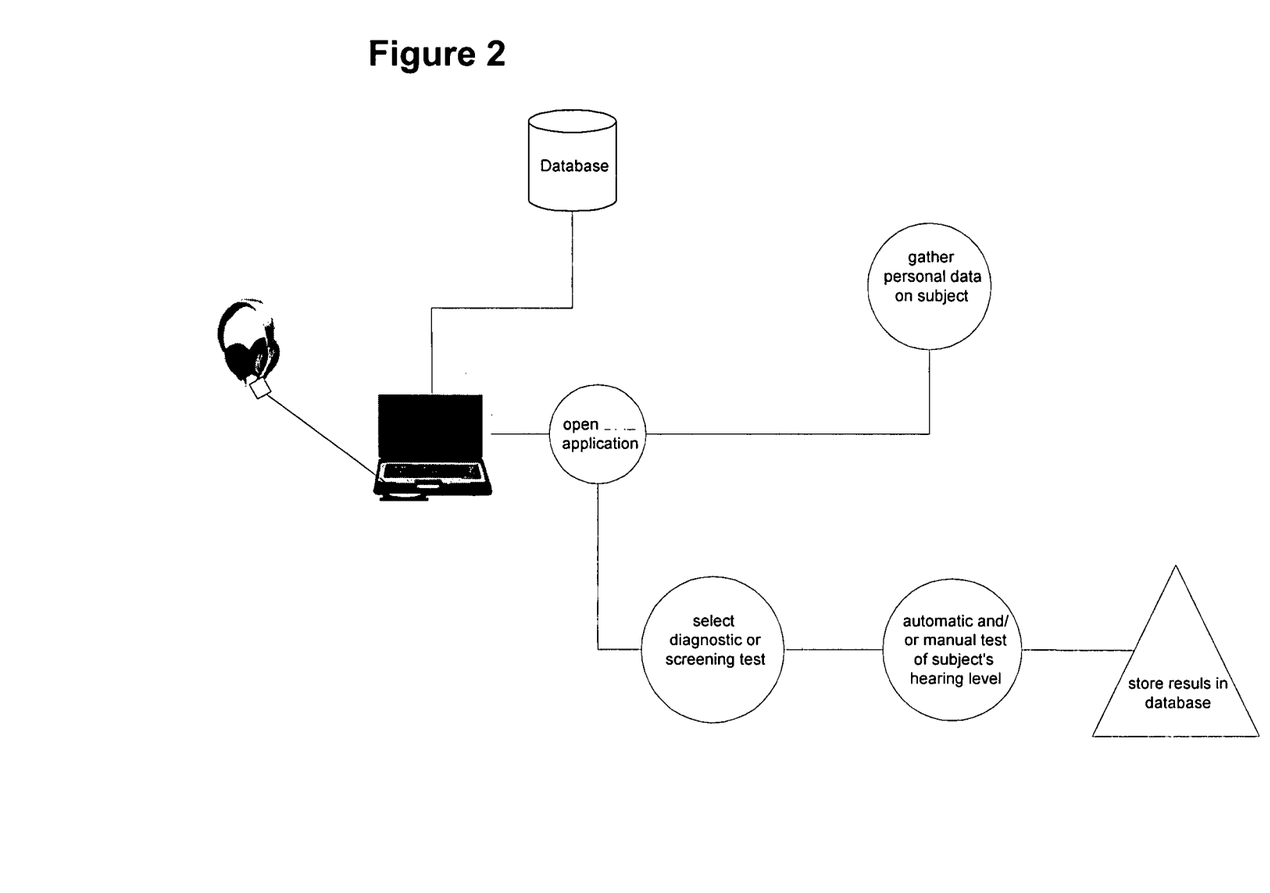
FIG. 2 shows schematically the steps in performing an audiometric test according to the present invention.

Having completed a general overview, key aspects of the system will now be described in greater detail. Referring to FIG. 2, in performing the audiometric test the desired sounds or tones, at a frequency and loudness level prescribed by the test protocol (for example, according to Class 1 audiometer standards), are digitally encoded as data by the software. The tones are produced using bespoke software which combines to produce any wave format and amplitude or combination thereof in any predefined, manual or automatically generated test sequence. The digital data relating to the desired sound is then sent to a calibrated digital headset or headphone comprising at least one speaker, preferably of audiometric test quality. Alternative embodiments of the digital headset include, for example, a bone vibrator, means to provide oroecustic emissions or means to measure brain stem response. The system is also capable of producing a masking sound in one ear while the other ear is being tested with the masking levels being selected either manually or automatically, for example to prevent the test sound from being heard using the test recipient's other ear. The subject undergoing the test feeds back a signal to the computer indicating the threshold of hearing for the tones received through the headset. This produces a graph or audiogram which shows the profile of the subject's hearing threshold across the audio frequency band for each ear. The audiograms, in addition to any additional desired data on the subject, are stored locally in a database that is optionally uploaded to a central data repository when a computer network is available.

The loudness levels and tones which are sent to the system have both automatic and manual control and can readily be set to any international hearing test/screening standard, protocol or methodology. The headset is capable of emitting sounds having a volume up to and exceeding (if necessary) 120 dBHL. The set of frequencies and loudness levels can be selected based on the subject's previous feedback so as to obtain higher resolution information concerning the hearing profile in specified regions (e.g. regions of rapid change of hearing threshold). This is particularly useful in further characterizing a region of hearing loss between two or more specified test frequencies and allows the exact region of hearing loss to be digitally discriminated. The system can automatically granulate and target tones to the area of the audio frequency band where the subject has the most impaired hearing loss. This enables more accurate diagnosis of the hearing loss/impairment and also allows hearing aids and other hearing enhancing devices to be better tailored and tuned to the precise frequencies and amplification levels required by the subject.

The computer can be used to operate and control in parallel a multitude of calibrated sound and/or vibration reproduction systems and so perform parallel audiometric testing and data capture of many subjects at the same time. This feature is particularly suited to industrial or institutional audiometric screening or to audiology clinics where many subjects need to be tested.

Calibration of the digital headset is an important factor in obtaining accurate test results. The headset is normally calibrated at a certified test and measurement standards laboratory, although on-site calibration can also be performed with appropriate mobile equipment. The calibration consists of measuring the frequency and volume response of the speakers to varying analog electrical input signals. The analog electrical input signals comprise variable voltage signals that are either time or frequency discriminated. The digital headset can be manually calibrated for any frequency and volume level within its operating range. In one embodiment, the headset includes a recalibration means to automatically recalibrate itself at any interval including both before and after each hearing test using a digital reference standard stored either on the headset or on the computer to which it is connected. The recalibration means optionally includes a warning indicator to alert the operator if recalibration is required. The recalibration means comprises, for example, a microphone or plurality of microphones, preferably calibrated microphones, that receive sound outputs from the speaker(s) of the headset and provide those sound outputs to the computer via an analog to digital (A/D) converter. The microphone input is digitally compared with a pre-recorded baseline established immediately following headset calibration. Differences in the comparison exceeding a threshold tolerance can be used to flag the need for re-calibration of the headset. A log of the comparison results can be kept for trend analysis to predict when calibration should be performed. In this manner, the calibration status of the headset can be periodically monitored to ensure quality control of the audiometric test results.

Unlike current audiometers, where the audiometer, headset, electrical leads, etc. need calibration as a total system, in the present invention only the digital headset requires calibration. Since any number of headsets are interchangable with any particular computer, the test apparatus need not necessarily be taken out of commission during recalibration so long as more than one calibrated headset is kept on-hand. In addition, a digital correction can be applied to somewhat counteract the effects of calibration drift. The digital correction is determined based on the digital comparison obtained in the recalibration procedure described above and causes the computer to modify its instructions to the headset in order to restore the emitted sounds to within calibration tolerances. This digital correction can be especially useful when the headset is being used in conjunction with a hearing profile, as the digital correction can then be targeted to the region(s) of hearing loss to prolong the interval between certified calibrations.

Figure 3:
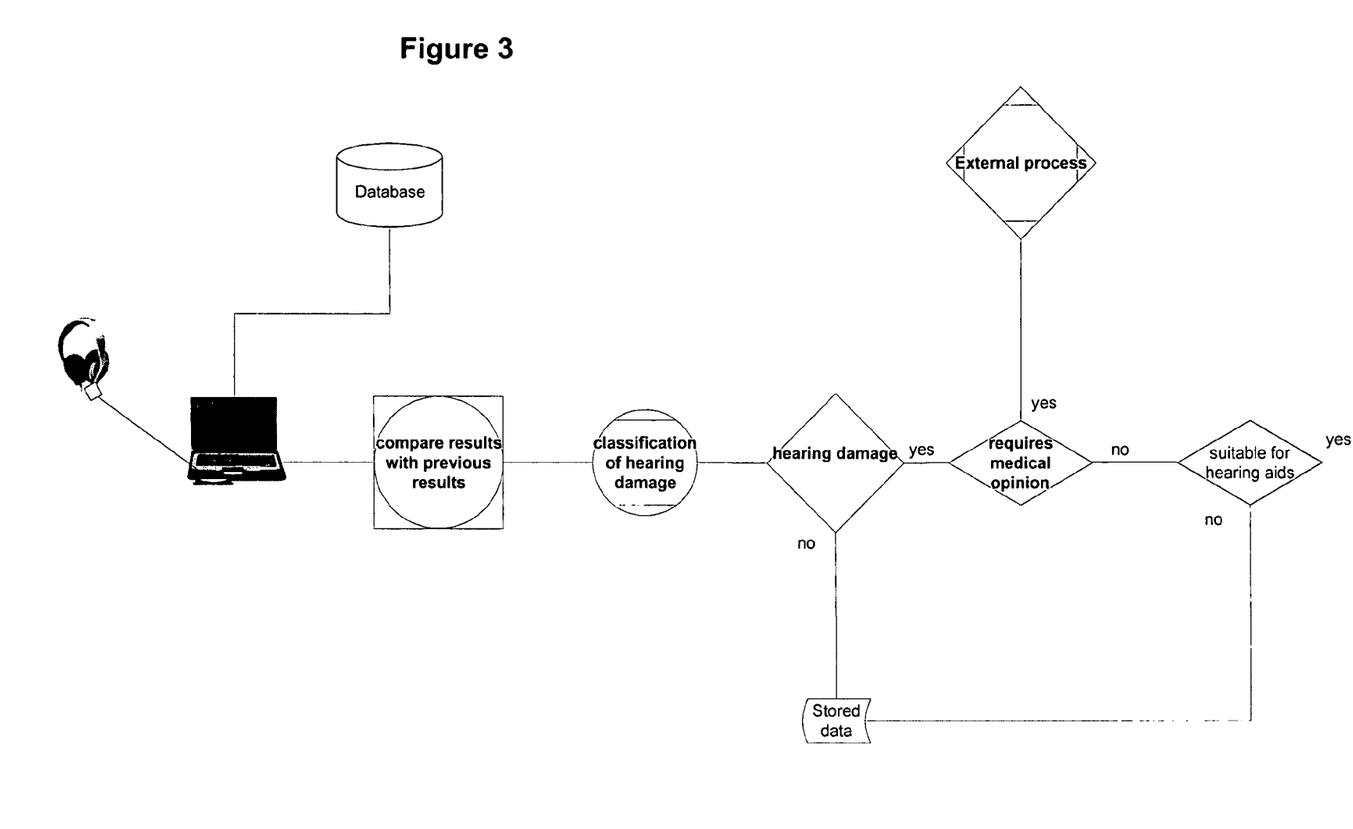
FIG. 3 shows schematically the steps in conducting a computerized diagnosis of hearing loss and the computerized analysis of the test results.

Referring now to FIG. 3, in automatically analyzing the audiograms to produce an electronic user hearing profile, the computer first compares the most recent audiogram with any previous audiogram of the subject and a manual and/or automated diagnosis is made of the severity of hearing loss/damage. Where appropriate, the audiometric data is uploaded to a central server and made available to an appropriate healthcare professional for further analysis.

Figure 4:
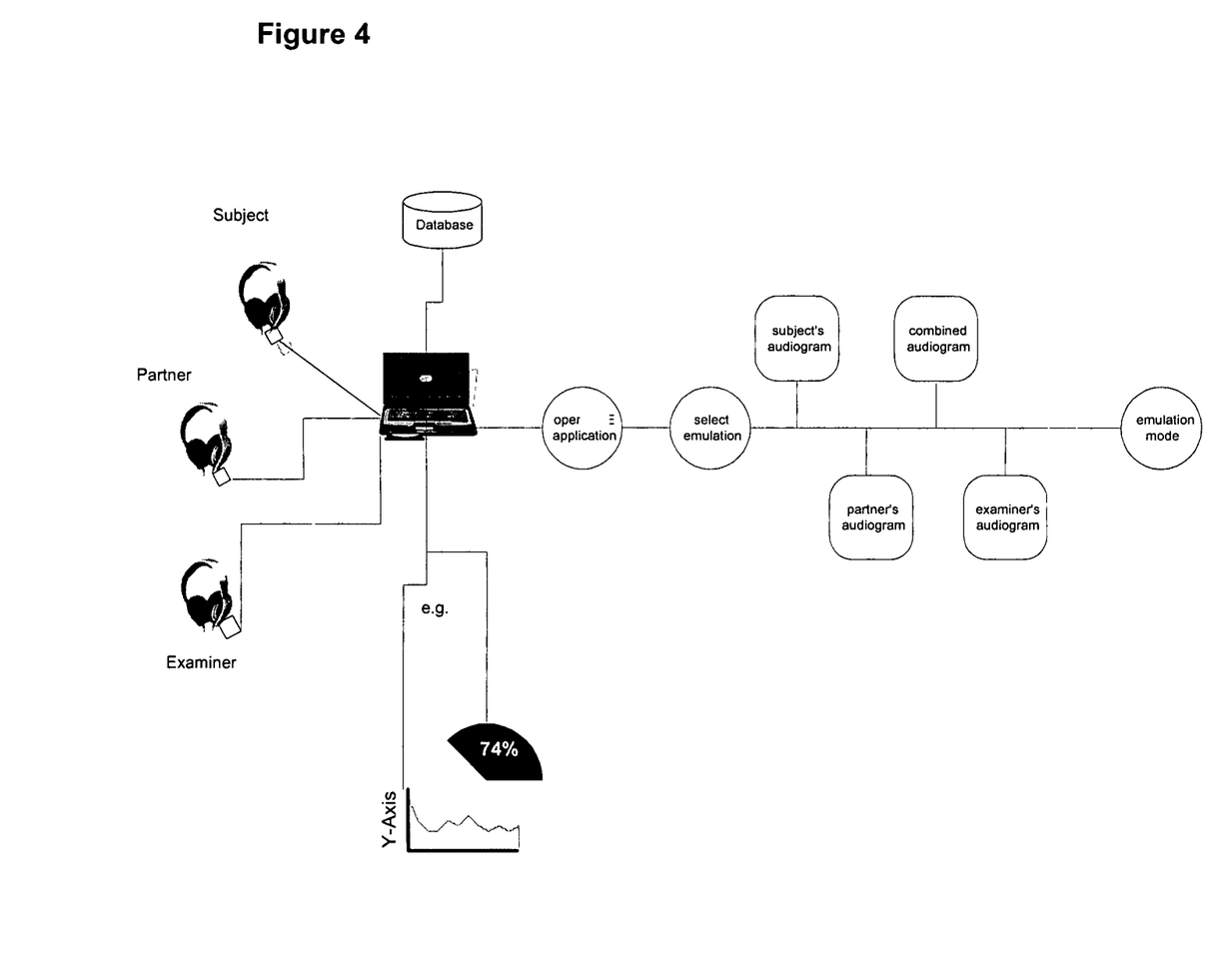
FIG. 4 shows schematically the steps in performing an emulation of how sounds are perceived by a user based upon both a user hearing profile and a partner hearing profile; and, FIG. 5 shows schematically the interconnection of elements of the digital headset.

Referring to FIG. 4, in emulating for a partner how sounds are perceived by a user, the user hearing profile is overlaid on the partner hearing profile and the two profiles are compared. The computer is then able to determine the required amount of amplification or deamplification of a particular frequency that is required to align the partner hearing profile with the user hearing profile. These amplifications can then be used in emulating for the partner how sounds are perceived by the user, either with pre-recorded sounds or in real-time (particularly useful for live speech). The emulation facility also allows the user to experience the effective of a hearing aid immediately, without having to wait for the hearing aid to first be made. The emulation facility also permits a greater or lesser degree of amplification of any frequency for a variety of sound environments to be experienced by the user in an effort to fine tune the hearing aid design prior to ordering. The system is capable of emulating different types of hearing aids, for example using the specifications of commercially available hearing aids as provided by their supplier. This enables a hearing aid or other sound enhancing device to be programmed so as to optimise the subjects listening experience.

For the benefit of the subject and/or the partner, the system can visually represent the subject's hearing loss and visually represent the improvement to the subject's hearing provided by any particular type of hearing aid. This representation of the hearing loss can be visually demonstrated in relation to the subjects' inner ear or cochlea, thereby highlighting the relationship of the actual damage to the audiogram test results. Both the audio and visual representations of improvement can be experienced at the same time. These emulation and visual representation features are expected to increase the likelihood of a hearing aid purchase and to reduce the overall sales cycle lead time by providing immediate comparative feedback to both the test recipient and the partner.

There are a considerable number of people who have some hearing loss, but who have not yet reached the stage where a hearing aid is required. As a consequence, these people are not able to experience the full range of sounds in their daily life. They tend to either accept this inconvenience or else turn up the volume of their sound producing devices, thereby exacerbating their hearing damage and potentially causing damage or annoyance to those around them.

The hearing profile relates the frequency and volume information of sounds as heard by the test recipient to the frequency and volume information of sounds as emitted by the audiometric test system. The calibration reference relates analog electrical input signals with frequency and volume characteristics of sound outputs from the speaker(s). The hearing profile can therefore be used in conjunction with the calibration reference to relate the frequency and volume information of sounds as heard by the test recipient with the analog electrical input signal required to generate those sounds. A correction to the analog electrical input signal can be calculated for frequencies within the range of a test recipient's hearing loss to cause the headset to emit sounds at a volume level sufficient to be heard by the test recipient. This correction can be uploaded to the headset, or any other suitable audio emitting device, allowing the headset or device to compensate for the user's hearing loss. The uploading of hearing correction information can be completed either from the computer that was used to perform the hearing test and generate the user hearing profile or over a network. In certain applications, such as voice over IP telephony, it is often desirable to have the hearing modification performed by a computer or over a computer network rather than by a headset or other audio emitting device containing the uploaded hearing correction information. In this case, the hearing profile and/or audio correction information can be stored on a server accessible over a telecommunications network and indexed in relation to a personal identifier, for example a pin code or other access code. Once the personal identifier has been entered, all further broadcasts of audio information over the transmission network can be corrected by the server in order to produce an audio output that is tailored to the specific needs of the listener.

Figure 5:
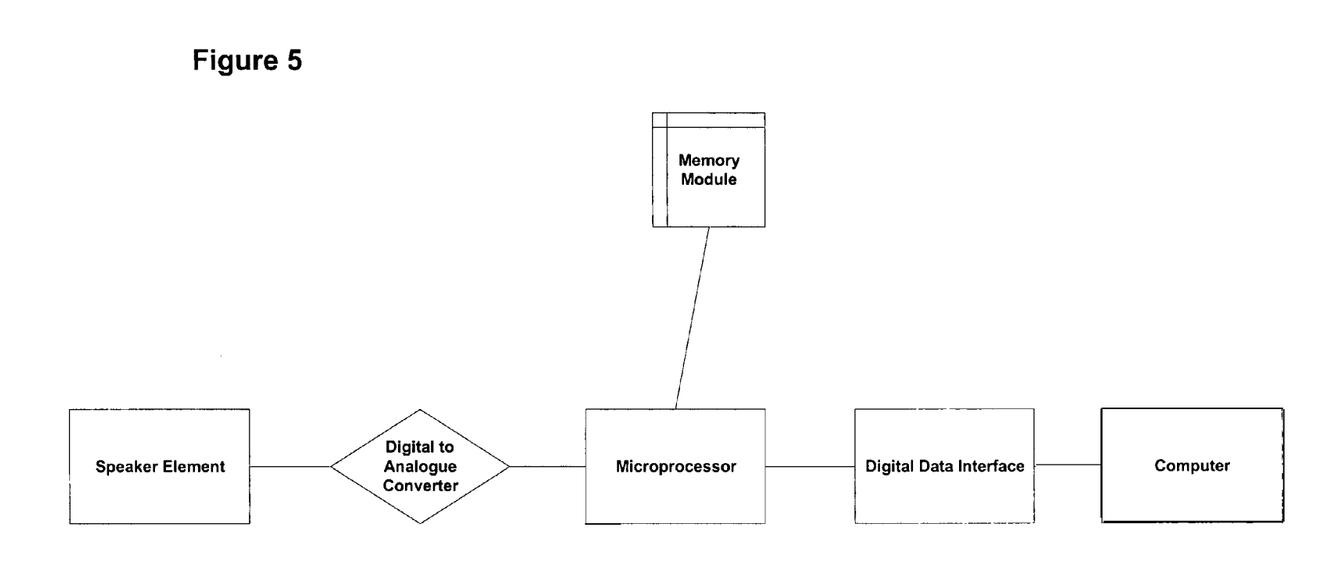

Referring to FIG. 5, the various elements of the digital headset and their interconnection with one another are shown schematically. A computer running appropriate software provides digital signals to the headset via a digital data interface (eg: USB port, wireless connection, etc.) The digital signals represent sounds that the software is instructing the headset to accurately reproduce. In one embodiment, these digital signals are pre-corrected by a microprocessor located within the computer using a unique calibration reference stored within a memory module (eg: EEPROM) located on the headset. In another embodiment, the digital signals are optionally stored in a digital data buffer and are ultimately received by a microprocessor located on the headset. The microprocessor uses the unique calibration reference to determine the analog signal required to illicit an exact reproduction from the speaker(s) of the sound requested by the computer. A temporary variable storage buffer is utilized by the microprocessor while making this determination. The calibration reference comprises either the actual information relating analog input signals to audible output signals or a unique identifier for use in retrieving such information from another storage location. A digital signal processor (DSP) is optionally provided between the microprocessor and digital to analog converter, or is incorporated with the microprocessor, and utilized in determining the required analog signal. The microprocessor and/or DSP then instruct the digital to analog converter to deliver the analog signal to the speaker(s). The digital to analog converter can be of any suitable configuration (eg: 8 bit, 16 bit, 24 bit, etc.). The speaker(s) then emit an exact reproduction of the sound requested by the computer. When used during audiometric testing, this sound can be a pure tone or any other suitable sound for test purposes. When the headset is used as a hearing corrective device, the user's hearing profile or correction information derived from the user's hearing profile is either stored on the headset (for example, within the memory module or within another memory module provided for that purpose), or stored on the computer and utilized by the software in creating a digital signal for requesting an exact sound from the headset. Although described with reference to individual physical elements, some or all of the functions of the foregoing can be provided by one or more ASIC's. The physical elements are located either on the headset itself, for example on a head-mountable housing of the headset, or within a small enclosure that is inline between the digital data interface and the housing. The latter is particularly amenable to cabled connections between the computer and headset, whereas the former is particularly amenable to wireless implementations.

The elements of the headset system are also provided as part of a kit that comprises at least the enclosure and instructions for the interconnection of the enclosure, housing and computer. The kit optionally comprises the housing, computer and/or software, along with instructions for use thereof.

The foregoing describes preferred embodiments of the invention and other features and embodiments of the invention will be evident to persons skilled in the art. The following claims are to be construed broadly with reference to the foregoing and are intended by the inventor to include other variations and sub-combinations even if not explicitly claimed

The invention claimed is:
1. A method of audiometric testing using a calibrated headset, the method comprising:
 a) providing a calibrated headset comprising:
  i) at least one speaker;
  ii) a digital data interface adapted for connection with a computer;
  iii) an electronic memory module adapted for storing a unique calibration reference relating to the said at least one speaker, the said unique calibration reference relating analog electrical input signals which can be delivered to the at least one speaker with frequency and volume characteristics of sound outputs from said at least one speaker;
  iv) a microprocessor adapted for processing digital data received from said computer via the said interface, the said digital data corresponding to a desired sound output, the microprocessor adapted to electronically access the said unique calibration reference to determine the analog signal to be delivered to the said at least one speaker in order to emit the said desired sound output, the said unique calibration reference being required to illicit an exact reproduction from the said at least one speaker of the sound output; and,
  v) a digital to analog converter adapted for converting the said digital data processed by the microprocessor to the analog signal and adapted for delivering the analog signal to the said at least one speaker;
 b) interconnecting the said digital data interface with the computer;
 c) administering a software generated audiometric test using the said calibrated digital headset the test comprising the emission of a first set of sound outputs having pre-specified frequency and/or volume characteristics;
 d) receiving into the said computer user feedback concerning the audibility of the first set of sound outputs;
 e) generating using the said computer a user hearing profile based upon the results of one or more audiometric tests;
 f) analyzing the user hearing profile with the computer to determine at least one region of hearing loss;
 g) comparing the user hearing profile with a previously determined partner hearing profile using the computer;
 h) for the partner hearing profile, determining using the computer the required amplification or deamplification of frequencies within the region of hearing loss in order to match the partner hearing profile with the user hearing profile; and i) using the digital headset, emitting a series of sounds modified by the required amplification or deamplification in order to audibly emulate for the partner how those sounds are perceived by the user.

2. The method according to claim 1, wherein the method further comprises:
   j) administering a follow-up audiometric test using the headset, the follow-up audiometric test comprising the emission of a second set of sound outputs having frequency and/or volume characteristics selected by the computer to further characterize a region of hearing loss within the user hearing profile;
   k) receiving into the computer user feedback concerning the audibility of the second set of sound outputs; and
   l) refining with the computer the user hearing profile based upon the results of one or more follow-up audiometric tests.

3. The method according to claim 2, wherein the second set of sound outputs comprises a plurality of discrete frequencies selected from between the frequencies employed in the first set of sound outputs.

4. The method according to claim 1, wherein the method further comprises reprogramming the digital headset using the user hearing profile to function as a customized headset by:
   j) analyzing the user hearing profile with the computer to determine at least one region of hearing loss;
   k) determining using the computer the required amplification of frequencies within the region of hearing loss;
   l) uploading the required amplification to the headset using the digital data interface; and,
   m) electronically storing the required amplification on the digital headset in a data format accessible by the microprocessor.

5. The method according to claim 1, wherein the method further comprises:
   j) providing a microphone interconnected with an A/D converter for digitally delivering sound information to the computer;
   k) digitally recording speaker outputs using the microphone; and
   l) comparing the digitally recorded outputs with a baseline of recordings established following calibration of the speaker to determine the need for re-calibration of the headset.

6. The method according to claim 5, wherein the method further comprises obtaining a digital correction from the comparison conducted in step l) and applying the digital correction within the computer or the headset to counteract the need for headset re-calibration.

7. The method according to claim 1, wherein the method further comprises uploading the user hearing profile to a central server accessible to healthcare professionals.

8. The method according to claim 1, wherein the method further comprises uploading the user hearing profile to a central server accessible to a hearing aid manufacturer and electronically ordering a customized hearing aid device based upon the user hearing profile.

9. The method according to claim 1, wherein the method further comprises reprogramming an audio emitting digital device using the user hearing profile to function as a customized audio emitting digital device by:
   j) analyzing the user hearing profile with the computer to determine at least one region of hearing loss;
   k) determining using the computer the required amplification of frequencies within the region of hearing loss; and
   l) applying the required amplification to audio outputs of the audio emitting device.

10. The method according to claim 9, wherein the method further comprises:
    m) uploading the required amplification to the audio emitting digital device;
    n) electronically storing the required amplification on the audio emitting digital device in a data format accessible by audio processing circuitry of the device; and
    o) applying the required amplification to audio outputs of the audio emitting device using the audio processing circuitry of the device.

11. The method according to claim 9, wherein the method further comprises:
    m) uploading the required amplification to a server on an audio transmission network;
    n) relating the required amplification to a personal identifier that can be received by the server; and
    o) applying the required amplification to signals transmitted over the network to a user providing the personal identifier.

* * * * *